United States Patent
Gerard et al.

(10) Patent No.: US 10,463,693 B2
(45) Date of Patent: Nov. 5, 2019

(54) SURFACE-REACTED CALCIUM CARBONATE FOR DESENSITIZING TEETH

(71) Applicant: Omya International AG, Oftringen (CH)

(72) Inventors: Daniel E. Gerard, Basel (CH); Tanja Budde, Brittnau (CH); Joachim Schoelkopf, Oberkulm (CH); Patrick A. C. Gane, Rothrist (CH)

(73) Assignee: Omya International AG, Blue Ash, OH (US)

( * ) Notice: Subject to any disclaimer, the term of this patent is extended or adjusted under 35 U.S.C. 154(b) by 0 days.

(21) Appl. No.: 15/123,034

(22) PCT Filed: Mar. 20, 2015

(86) PCT No.: PCT/EP2015/055962
§ 371 (c)(1),
(2) Date: Sep. 1, 2016

(87) PCT Pub. No.: WO2015/140308
PCT Pub. Date: Sep. 24, 2015

(65) Prior Publication Data
US 2017/0157171 A1    Jun. 8, 2017

(30) Foreign Application Priority Data
Mar. 21, 2014   (EP) .................................... 14161064

(51) Int. Cl.
*A61Q 11/00* (2006.01)
*A61K 8/02* (2006.01)
*A61K 6/00* (2006.01)
*A61K 33/10* (2006.01)
*A61K 8/19* (2006.01)

(52) U.S. Cl.
CPC ............... *A61K 33/10* (2013.01); *A61K 6/00* (2013.01); *A61K 6/0017* (2013.01); *A61K 8/19* (2013.01); *A61Q 11/00* (2013.01)

(58) Field of Classification Search
CPC .............. A61Q 11/00; A61K 2800/412; A61K 8/0241; A61K 6/00; A61K 6/0008
See application file for complete search history.

(56) References Cited

U.S. PATENT DOCUMENTS

| | | | |
|---|---|---|---|
| 5,240,696 A | 8/1993 | Van Der Ouderaa et al. | |
| 8,658,139 B1 | 2/2014 | Cutler | |
| 2002/0001568 A1* | 1/2002 | Thomas | A61K 8/25 424/49 |
| 2004/0020410 A1 | 2/2004 | Gane et al. | |
| 2007/0258916 A1* | 11/2007 | Ferracane | A61K 8/25 424/57 |
| 2008/0112901 A1* | 5/2008 | MacDonald | A61K 8/19 424/52 |
| 2009/0202451 A1 | 8/2009 | Prencipe et al. | |
| 2012/0014883 A1* | 1/2012 | Scott | A61K 8/0216 424/52 |
| 2012/0052023 A1* | 3/2012 | Gane | A61K 9/145 424/49 |

FOREIGN PATENT DOCUMENTS

| | | |
|---|---|---|
| EP | 1974806 A1 | 10/2008 |
| EP | 1974807 A1 | 10/2008 |
| EP | 1982759 A1 | 10/2008 |
| EP | 2070991 A1 | 6/2009 |
| EP | 2168572 A1 | 3/2010 |
| EP | 2264108 A1 | 12/2010 |
| EP | 2578272 A1 | 4/2013 |
| EP | 2719373 A1 | 4/2014 |
| JP | 2003073246 A | 3/2003 |
| WO | 0010520 A1 | 3/2000 |
| WO | 0039222 A1 | 7/2000 |
| WO | 0078270 A1 | 12/2000 |
| WO | WO 0158416 A2 * | 8/2001 ........... A61K 8/0283 |
| WO | 03/026601 A1 | 4/2003 |
| WO | 2010037753 A1 | 4/2010 |
| WO | 2010115041 A2 | 10/2010 |
| WO | 2012143220 A1 | 10/2012 |
| WO | 2014023466 A1 | 2/2014 |

OTHER PUBLICATIONS

International Search Report dated Jun. 16, 2015 for PCT/EP2015/055962.
Written Opinion of the International Searching Authority dated Jun. 16, 2015 for PCT/EP2015/055962.
Hirayama et al., "Effects of Calcium Carbonate on Odontoblast Differentiation and Calcification Ability of Human Dental Pulp Cells," J. Oral Tissue Engin., vol. 11, No. 2, 2013, pp. 123-134.

* cited by examiner

*Primary Examiner* — Tracy Liu
(74) *Attorney, Agent, or Firm* — Schwegman Lundberg & Woessner, P.A.

(57) ABSTRACT

The present invention relates to surface-reacted calcium carbonate, wherein the surface-reacted calcium carbonate is a reaction product of natural or synthetic calcium carbonate with carbon dioxide and at least one acid. Said calcium carbonate and oral compositions containing the same can be used as a medicament, and especially in treating dentine hypersensitivity.

20 Claims, 8 Drawing Sheets

SURFACE-REACTED CALCIUM CARBONATE FOR DESENSITIZING TEETH

CROSS-REFERENCE TO RELATED APPLICATIONS

This is a U.S. national phase of PCT Application No. PCT/EP2015/055962, filed Mar. 20, 2015, which claims priority to European Application No. 14161064.2, filed Mar. 21, 2014.

The present invention relates to new desensitizing agents for hypersensitive teeth and oral care compositions including such agents and their use.

Dentine is calcified tissue of the body, and along with enamel, cementum, and pulp is one of the four major components of teeth. It is usually covered by enamel on the crown and cementum on the root and surrounds the entire pulp. Dentine consists of microscopic channels, called dentinal tubules, which radiate outward through the dentine from the pulp to the exterior cementum or enamel border.

Dentine hypersensitivity is a common clinical condition usually associated with exposed dentine surfaces. Many diseases, including physiological wear, and enamel hypoplasia, wedge shaped defects, and gingival recession, can lead to exposed dentine. It can affect patients of any age group and most commonly affects the canines and premolars of both the arches. Dentine hypersensitivity is characterised by typical short sharp pain on the exposed dentine which is aroused by thermal, evaporative, tactile, osmotic or chemical stimuli.

Currently, the most widely accepted mechanism of dentine hypersensitivity is the hydrodynamic theory advanced by Brännström in the 1960s. According to said theory, dentine hypersensitivity occurs when the external stimulus such as temperature or a physical or osmotic pressure change contacts exposed dentine and triggers a change in the flow of dentinal fluid. The resultant pressure change across the dentine activates internal nerve fibres to cause immediate pain. Therefore, one approach to treat dentine hypersensitivity is based on the occlusion of dentinal tubules with materials, reducing dentine permeability, and reducing or preventing dentine fluid flow due to external stimuli.

Oral compositions for treating hypersensitive teeth comprising bioactive glass and one or more bioadhesive active components are disclosed in WO 2010/115041. EP 2 578 272 A1 is concerned with a formulation for oral teeth, comprising a plurality of calcium ion carriers, and a plurality of calcium-containing particulates, wherein the calcium-containing particulates are carried by the calcium ion carriers. The effects of dentifrice containing hydroxyapatite on dentinal tubule occlusion is studied in Yuan et al., PLOS ONE 2012, 7(12), 1-8. However, all of these occlusion agents may lead to a complete blocking of the dentinal tubules, which would cut of the flow of nutrients which are supplied daily to each tubule by the artery that accompanies the nerve and vein in the root canal and keeps the teeth alive and healthy.

In view of the foregoing, there is a continuous need for agents that are useful in the treatment of dentine hypersensitivity.

Accordingly, it is an object of the present invention to provide a desensitizing agent that can be used in the treatment of dentine hypersensitivity. In particular, it is desirable to provide a desensitizing agent that is easy to apply, can provide instant relief and is consistently effective. It is also desirable to provide a desensitizing agent that is non-toxic, non-irritant to the pulp, and painless on application.

It is also an object of the present invention to provide a desensitizing agent that can migrate into the dentine tubules easily and remains in the tubules and occludes the tubules effectively for a long period after application. It is also desirable to provide a desensitizing agent that allows a diffuse flow of nutrients into the dentine tubules without allowing hydrodynamic flow, which can cause pain. Furthermore, it is desirable to provide a desensitizing agent that is more resistant to acid challenge.

The foregoing and other objects are solved by the subject-matter as defined herein in the independent claims.

According to one aspect of the present invention, a surface-reacted calcium carbonate for use as a medicament is provided, wherein the surface-reacted calcium carbonate is a reaction product of natural or synthetic calcium carbonate with carbon dioxide and at least one acid.

According to another aspect of the present invention, surface-reacted calcium carbonate for use in treating dentine hypersensitivity is provided, wherein the surface-reacted calcium carbonate is a reaction product of natural or synthetic calcium carbonate with carbon dioxide and at least one acid.

According to still another aspect of the present invention, an oral care composition for use as a medicament is provided, comprising a surface-reacted calcium carbonate, wherein the surface-reacted calcium carbonate is a reaction product of natural or synthetic calcium carbonate with carbon dioxide and at least one acid.

According to still another aspect of the present invention, an oral care composition for use in treating dentine hypersensitivity is provided comprising a surface-reacted calcium carbonate, wherein the surface-reacted calcium carbonate is a reaction product of natural or synthetic calcium carbonate with carbon dioxide and at least one acid.

According to still another aspect of the present invention, an oral care composition comprising a surface-reacted calcium carbonate is provided, wherein the surface-reacted calcium carbonate is a reaction product of natural or synthetic calcium carbonate with carbon dioxide and at least one acid, and wherein the surface-reacted calcium carbonate is in form of particles having a volume determined top cut particle size ($d_{98}$) of equal to or less than 6 µm.

Advantageous embodiments of the present invention are defined in the corresponding sub-claims.

According to one embodiment the at least one acid is selected from the group consisting of hydrochloric acid, sulphuric acid, sulphurous acid, phosphoric acid, citric acid, oxalic acid, acetic acid, formic acid, and mixtures thereof, preferably the at least one acid is selected from the group consisting of hydrochloric acid, sulphuric acid, sulphurous acid, phosphoric acid, oxalic acid, and mixtures thereof, and more preferably the at least one acid is phosphoric acid.

According to one embodiment the surface-reacted calcium carbonate is in form of particles having a volume median grain diameter ($d_{50}$) of equal to or less than 3 µm, preferably from 1.5 to 2.9 µm, more preferably from 1.7 to 2.7 µm, and most preferably from 2.2 to 2.6 µm, and/or a volume determined top cut particle size ($d_{98}$) of equal to or less than 6 µm, preferably from 3.5 to 5.5 µm, and more preferably from 4.5 to 5 µm. According to another embodiment the surface-reacted calcium carbonate is in form of particles having a specific surface area of from 5 $m^2/g$ to 200 $m^2/g$, more preferably 20 $m^2/g$ to 80 $m^2/g$, and even more preferably 30 $m^2/g$ to 60 $m^2/g$, measured using nitrogen and the BET method according to ISO 9277.

According to one embodiment at least one active agent is associated with the surface-reacted calcium carbonate, preferably the active agent is at least one additional desensitizing agent, and more preferably the at least one additional desensitizing agent is selected from the group consisting of potassium nitrate, gluteraldehyde, silver nitrate, zinc chloride, strontium chloride hexahydrate, sodium fluoride, stannous fluoride, strontium chloride, strontium acetate, arginine, hydroxyapatite, calcium sodium phosphosilicate, potassium oxalate, calcium phosphate, calcium carbonate, bioactive glasses, and mixtures thereof.

According to one embodiment the surface-reacted calcium carbonate is obtained by a process comprising the steps of:
 a) providing a suspension of natural or synthetic calcium carbonate,
 b) adding at least one acid having a $pK_a$ value of 0 or less at 20° C. or having a $pK_a$ value from 0 to 2.5 at 20° C. to the suspension of step a), and
 c) treating the suspension of step a) with carbon dioxide before, during or after step b).

According to another embodiment the surface-reacted calcium carbonate is obtained by a process comprising the steps of:
 A) providing a natural or synthetic calcium carbonate,
 B) providing at least one water-soluble acid,
 C) providing gaseous $CO_2$,
 D) contacting said natural or synthetic calcium carbonate of step A) with the at least one acid of step B) and with the $CO_2$ of step C),
 characterised in that:
 i) the at least one acid of step B) has a $pK_a$ of greater than 2.5 and less than or equal to 7 at 20° C., associated with the ionisation of its first available hydrogen, and a corresponding anion is formed on loss of this first available hydrogen capable of forming a water-soluble calcium salt, and
 ii) following contacting the at least one acid with natural or synthetic calcium carbonate, at least one water-soluble salt, which in the case of a hydrogen-containing salt has a $pK_a$ of greater than 7 at 20° C., associated with the ionisation of the first available hydrogen, and the salt anion of which is capable of forming water-insoluble calcium salts, is additionally provided.

According to one embodiment the oral care composition comprises from 1 to 20 wt.-%, preferably from 1.5 to 15 wt.-%, more preferably from 2 to 10 wt.-% of the surface-reacted calcium carbonate, based on the total weight of the composition. According to another embodiment the oral care composition is a toothpaste, a toothpowder, or a mouthwash, and wherein preferably the surface-reacted calcium carbonate is a reaction product of natural or synthetic calcium carbonate with carbon dioxide and phosphoric acid.

According to one embodiment the oral care composition comprises at least one additional desensitising agent, preferably selected from the group consisting of potassium nitrate, gluteraldehyde, silver nitrate, zinc chloride, strontium chloride hexahydrate, sodium fluoride, stannous fluoride, strontium chloride, strontium acetate, arginine, hydroxyapatite, calcium sodium phosphosilicate, potassium oxalate, calcium phosphate, calcium carbonate, bioactive glasses, and mixtures thereof. According to another embodiment the oral care composition comprises a bioadhesive polymer, preferably selected from the group consisting of hydroxyethyl methacrylate, PEG/PPG copolymers, polyvinylmethylether/maleic anhydride copolymers, polyvinylpyrrolidone (PVP), cross-linked PVP, shellac, polyethylene oxide, methacrylates, acrylates copolymers, methacrylic copolymers, vinylpyrrolidone/vinyl acetate copolymers, polyvinyl caprolactum, polylactides, silicone resins, silicone adhesives, chitosan, milk proteins (casein), amelogenin, ester gum, and combinations thereof.

According to one embodiment the surface-reacted calcium carbonate has a radioactive dentine abrasion (RDA) value of less than 70, preferably less than 50, and more preferably less than 35. According to another embodiment the oral care composition has a pH between 7.5 and 10, preferably between 8 and 9.

It should be understood that for the purpose of the present invention, the following terms have the following meaning.

For the purpose of the present invention, an "acid" is defined as Brønsted-Lowry acid, that is to say, it is an $H_3O^+$ ion provider. An "acid salt" is defined as an $H_3O^+$ ion-provider, e.g., a hydrogen-containing salt, which is partially neutralised by an electropositive element. A "salt" is defined as an electrically neutral ionic compound formed from anions and cations. A "partially crystalline salt" is defined as a salt that, on XRD analysis, presents an essentially discrete diffraction pattern.

In accordance with the present invention, $pK_a$, is the symbol representing the acid dissociation constant associated with a given ionisable hydrogen in a given acid, and is indicative of the natural degree of dissociation of this hydrogen from this acid at equilibrium in water at a given temperature. Such $pK_a$ values may be found in reference textbooks such as Harris, D. C. "Quantitative Chemical Analysis: $3^{rd}$ Edition", 1991, W.H. Freeman & Co. (USA), ISBN 0-7167-2170-8.

In the meaning of the present invention, the "radioactive dentine abrasion (RDA)" is a measure of the erosive effect of abrasives in toothpaste on tooth dentine. It involves using standardised abrasives compared against the test sample. The determination of this value is done by determining the activity while cleaning worn dentine which is radioactively marked by mild neutron irradiation. The values obtained depend on the size, quantity and surface structure of abrasive used in toothpastes. The RDA value is set by the standards DIN EN ISO 11609.

"Ground calcium carbonate" (GCC) in the meaning of the present invention is a calcium carbonate obtained from natural sources, such as limestone, marble, dolomite, or chalk, and processed through a wet and/or dry treatment such as grinding, screening and/or fractionating, for example, by a cyclone or classifier.

"Precipitated calcium carbonate" (PCC) in the meaning of the present invention is a synthesised material, obtained by precipitation following reaction of carbon dioxide and lime in an aqueous, semi-dry or humid environment or by precipitation of a calcium and carbonate ion source in water. PCC may be in the vateritic, calcitic or aragonitic crystal form.

For the purpose of the present invention, a "surface-reacted calcium carbonate" is a material comprising calcium carbonate and an insoluble, at least partially crystalline, non-carbonate calcium salt, preferably, extending from the surface of at least part of the calcium carbonate. The calcium ions forming said at least partially crystalline non-carbonate calcium salt originate largely from the starting calcium carbonate material that also serves to form the surface-reacted calcium carbonate core. Such salts may include OFF anions and/or crystal water.

In the meaning of the present invention "water-insoluble" materials are defined as materials which, when mixed with deionised water and filtered on a filter having a 0.2 μm pore size at 20° C. to recover the liquid filtrate, provide less than or equal to 0.1 g of recovered solid material following evaporation at 95 to 100° C. of 100 g of said liquid filtrate. "Water-soluble" materials are defined as materials leading to the recovery of greater than 0.1 g of recovered solid material following evaporation at 95 to 100° C. of 100 g of said liquid filtrate.

Throughout the present document, the "particle size" of a calcium carbonate and other materials is described by its distribution of particle sizes. The value $d_x$ represents the diameter relative to which x % by weight of the particles have diameters less than $d_x$. This means that the $d_{20}$ value is the particle size at which 20 wt.-% of all particles are smaller, and the $d_{75}$ value is the particle size at which 75 wt.-% of all particles are smaller. The $d_{50}$ value is thus the weight median particle size, i.e. 50 wt.-% of all grains are bigger or smaller than this particle size. For the purpose of the present invention the particle size is specified as weight median particle size $d_{50}$ unless indicated otherwise. For determining the weight median particle size $d_{50}$ value a Sedigraph can be used. For the purpose of the present invention, the "particle size" of surface-reacted calcium is described as volume determined particle size distributions. For determining the volume determined particle size distribution, e.g., the volume median grain diameter ($d_{50}$) or the volume determined top cut particle size ($d_{98}$) of surface-reacted calcium carbonate, a Malvern Mastersizer 2000 can be used. The weight determined particle size distribution may correspond to the volume determined particle size if the density of all the particles is equal.

A "specific surface area (SSA)" of a calcium carbonate in the meaning of the present invention is defined as the surface area of the calcium carbonate divided by its mass. As used herein, the specific surface area is measured by nitrogen gas adsorption using the BET isotherm (ISO 9277:2010) and is specified in $m^2/g$.

An "oral care composition" in the meaning of the present invention refers to a composition suitable for the use in the mouth and for veterinary and/or human applications but especially for use in applications for the human mouth.

For the purpose of the present invention, the term "viscosity" or "Brookfield viscosity" refers to Brookfield viscosity. The Brookfield viscosity is for this purpose measured by a Brookfield (Typ RVT) viscometer at 20° C.±2° C. at 100 rpm using an appropriate spindle and is specified in mPa·s.

A "suspension" or "slurry" in the meaning of the present invention comprises insoluble solids and water, and optionally further additives, and usually contains large amounts of solids and, thus, is more viscous and can be of higher density than the liquid from which it is formed.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

Where an indefinite or definite article is used when referring to a singular noun, e.g. "a", "an" or "the", this includes a plural of that noun unless something else is specifically stated.

Terms like "obtainable" or "definable" and "obtained" or "defined" are used interchangeably. This e.g. means that, unless the context clearly dictates otherwise, the term "obtained" does not mean to indicate that e.g. an embodiment must be obtained by e.g. the sequence of steps following the term "obtained" though such a limited understanding is always included by the terms "obtained" or "defined" as a preferred embodiment.

According to the present invention, a surface-reacted calcium carbonate is used as a medicament. The surface-reacted calcium carbonate is a reaction product of natural or synthetic calcium carbonate with carbon dioxide and at least one acid.

In the following the details and preferred embodiments of the inventive surface-reacted calcium carbonate will be set out in more details. It is to be understood that these technical details and embodiments also apply to the inventive method for producing the surface-reacted calcium carbonate as well as to the inventive compositions comprising the surface-reacted calcium carbonate.

The Surface-Reacted Calcium Carbonate

According to the present invention, the surface-reacted calcium carbonate is a reaction product of natural or synthetic calcium carbonate with carbon dioxide and at least one acid.

Natural (or ground) calcium carbonate (GCC) is understood to be a naturally occurring form of calcium carbonate, mined from sedimentary rocks such as limestone or chalk, or from metamorphic marble rocks. Calcium carbonate is known to exist mainly as three types of crystal polymorphs: calcite, aragonite and vaterite. Calcite, the most common crystal polymorph, is considered to be the most stable crystal form of calcium carbonate. Less common is aragonite, which has a discrete or clustered needle orthorhombic crystal structure. Vaterite is the rarest calcium carbonate polymorph and is generally unstable. Natural calcium carbonate is almost exclusively of the calcitic polymorph, which is said to be trigonal-rhombohedral and represents the most stable of the calcium carbonate polymorphs. The term "source" of the calcium carbonate in the meaning of the present invention refers to the naturally occurring mineral material from which the calcium carbonate is obtained. The source of the calcium carbonate may comprise further naturally occurring components such as magnesium carbonate, alumino silicate etc.

According to one embodiment of the present invention, the natural calcium carbonate is selected from the group consisting of marble, chalk, dolomite, limestone and mixtures thereof.

According to one embodiment of the present invention the GCC is obtained by dry grinding. According to another embodiment of the present invention the GCC is obtained by wet grinding and optionally subsequent drying.

In general, the grinding step can be carried out with any conventional grinding device, for example, under conditions such that comminution predominantly results from impacts with a secondary body, i.e. in one or more of: a ball mill, a rod mill, a vibrating mill, a roll crusher, a centrifugal impact mill, a vertical bead mill, an attrition mill, a pin mill, a hammer mill, a pulveriser, a shredder, a de-clumper, a knife cutter, or other such equipment known to the skilled man. In case the calcium carbonate containing mineral material comprises a wet ground calcium carbonate containing mineral material, the grinding step may be performed under conditions such that autogenous grinding takes place and/or by horizontal ball milling, and/or other such processes known to the skilled man. The wet processed ground calcium carbonate containing mineral material thus obtained may be washed and dewatered by well-known processes, e.g. by flocculation, filtration or forced evaporation prior to drying. The subsequent step of drying may be carried out in a single step such as spray drying, or in at least two steps. It is also common that such a mineral material undergoes a beneficiation step (such as a flotation, bleaching or magnetic separation step) to remove impurities.

"Precipitated calcium carbonate" (PCC) in the meaning of the present invention is a synthesized material, generally obtained by precipitation following reaction of carbon dioxide and lime in an aqueous environment or by precipitation of a calcium and carbonate ion source in water or by precipitation of calcium and carbonate ions, for example $CaCl_2$ and $Na_2CO_3$, out of solution. Further possible ways of producing PCC are the lime soda process, or the Solvay process in which PCC is a by-product of ammonia production.

Precipitated calcium carbonate exists in three primary crystalline forms: calcite, aragonite and vaterite, and there are many different polymorphs (crystal habits) for each of these crystalline forms. Calcite has a trigonal structure with typical crystal habits such as scalenohedral (S-PCC), rhombohedral (R-PCC), hexagonal prismatic, pinacoidal, colloidal (C-PCC), cubic, and prismatic (P-PCC). Aragonite is an orthorhombic structure with typical crystal habits of twinned hexagonal prismatic crystals, as well as a diverse assortment of thin elongated prismatic, curved bladed, steep pyramidal, chisel shaped crystals, branching tree, and coral or worm-like form. Vaterite belongs to the hexagonal crystal system. The obtained PCC slurry can be mechanically dewatered and dried.

According to one embodiment of the present invention, the synthetic calcium carbonate is precipitated calcium carbonate, preferably comprising aragonitic, vateritic or calcitic mineralogical crystal forms or mixtures thereof.

According to one embodiment of the present invention, the natural or synthetic calcium carbonate is ground prior to the treatment with carbon dioxide and at least one acid. The grinding step can be carried out with any conventional grinding device such as a grinding mill known to the skilled person.

According to one embodiment of the present invention, the natural or synthetic calcium carbonate is in form of particles having a weight median particle size $d_{50}$ of equal to or less than 3 µm, preferably from 1.5 to 2.9 µm, more preferably from 1.7 to 2.7 µm, and most preferably from 2.2 to 2.6 µm. According to a further embodiment of the present invention, the natural or synthetic calcium carbonate is in form of particles having a top cut particle size $d_{98}$ of equal to or less than 6 µm, preferably from 3.5 to 5.5 µm, and more preferably from 4.5 to 5.0 µm.

Preferably the surface-reacted calcium carbonate to be used in the present invention is prepared as an aqueous suspension having a pH, measured at 20° C., of greater than 6.0, preferably greater than 6.5, more preferably greater than 7.0, even more preferably greater than 7.5.

In a preferred process for the preparation of the aqueous suspension of surface-reacted calcium carbonate, the natural or synthetic calcium carbonate, either finely divided, such as by grinding, or not, is suspended in water. Preferably, the slurry has a content of natural or synthetic calcium carbonate within the range of 1 wt.-% to 90 wt.-%, more preferably 3 wt.-% to 60 wt.-%, and even more preferably 5 wt.-% to 40 wt.-%, based on the weight of the slurry.

In a next step, at least one acid is added to the aqueous suspension containing the natural or synthetic calcium carbonate. The at least one acid can be any strong acid, medium-strong acid, or weak acid, or mixtures thereof, generating $H_3O^+$ ions under the preparation conditions. According to the present invention, the at least one acid can also be an acidic salt, generating $H_3O^+$ ions under the preparation conditions.

According to one embodiment, the at least one acid is a strong acid having a $pK_a$ of 0 or less at 20° C. According to another embodiment, the at least one acid is a medium-strong acid having a $pK_a$ value from 0 to 2.5 at 20° C. If the $pK_a$ at 20° C. is 0 or less, the acid is preferably selected from sulphuric acid, hydrochloric acid, or mixtures thereof. If the $pK_a$ at 20° C. is from 0 to 2.5, the acid is preferably selected from $H_2SO_3$, $H_3PO_4$, oxalic acid, or mixtures thereof. The at least one acid can also be an acidic salt, for example, $HSO_4^-$ or $H_2PO_4^-$, being at least partially neutralized by a corresponding cation such as $Li^+$, $Na^+$ or $K^+$, or $HPO_4^{2-}$, being at least partially neutralised by a corresponding cation such as $Li^+$, $Na^+$, $K^+$, $Mg^{2+}$ or $Ca^{2+}$. The at least one acid can also be a mixture of one or more acids and one or more acidic salts.

According to still another embodiment, the at least one acid is a weak acid having a $pK_a$ value of greater than 2.5 and less than or equal to 7, when measured at 20° C., associated with the ionisation of the first available hydrogen, and having a corresponding anion formed on loss of this first available hydrogen, which is capable of forming water-soluble calcium salts. According to the preferred embodiment, the weak acid has a $pK_a$ value from 2.6 to 5 at 20° C., and more preferably the weak acid is selected from the group consisting of acetic acid, formic acid, propanoic acid, and mixtures thereof.

In case a weak acid is used, after addition of said acid to the aqueous suspension containing the natural or synthetic calcium carbonate, at least one water-soluble salt, which in the case of a hydrogen-containing salt has a $pK_a$ of greater than 7, when measured at 20° C., associated with the ionisation of the first available hydrogen, and the salt anion of which is capable of forming water-insoluble calcium salts, is additionally added. The cation of said water-soluble salt is preferably selected from the group consisting of potassium, sodium, lithium and mixtures thereof. In a more preferred embodiment, said cation is sodium. It is of note that depending on the charge of the anion, more than one of said cations may be present to provide an electrically neutral ionic compound. The anion of said water-soluble salt is preferably selected from the group consisting of phosphate, dihydrogen phosphate, monohydrogen phosphate, oxalate, silicate, mixtures thereof and hydrates thereof. In a more preferred embodiment, said anion is selected from the group consisting of phosphate, dihydrogen phosphate, monohydrogen phosphate, mixtures thereof and hydrates thereof. In a most preferred embodiment, said anion is selected from the group consisting of dihydrogen phosphate, monohydrogen phosphate, mixtures thereof and hydrates thereof. Water-soluble salt addition may be performed dropwise or in one step. In the case of drop wise addition, this addition preferably takes place within a time period of 10 minutes. It is more preferred to add said salt in one step.

According to one embodiment of the present invention, the at least one acid is selected from the group consisting of hydrochloric acid, sulphuric acid, sulphurous acid, phosphoric acid, citric acid, oxalic acid, acetic acid, formic acid, and mixtures thereof. Preferably the at least one acid is selected from the group consisting of hydrochloric acid, sulphuric acid, sulphurous acid, phosphoric acid, oxalic acid, $H_2PO_4^-$, being at least partially neutralised by a corresponding cation such as $Li^+$, $Na^+$ or $K^+$, $HPO_4^{2-}$, being at least partially neutralised by a corresponding cation such as $Li^+$, $Na^+$, $K^+$, $Mg^{2+}$ or $Ca^{2+}$, and mixtures thereof, more preferably the at least one acid is selected from the group consisting of hydrochloric acid, sulphuric acid, sulphurous acid, phosphoric acid, oxalic acid, or mixtures thereof, and most preferably, the at least one acid is phosphoric acid. Without being bound to any theory, the inventors believe that the use of phosphoric acid can be beneficial in therapy, especially in treating dentine hypersensitivity.

The at least one acid can be added to the suspension as a concentrated solution or a more diluted solution. Preferably, the molar ratio of the at least one acid to the natural or synthetic calcium carbonate is from 0.05 to 4, more preferably from 0.1 to 2.

As an alternative, it is also possible to add the at least one acid to the water before the natural or synthetic calcium carbonate is suspended.

According to the present invention, the surface-reacted calcium carbonate is obtained by treating the natural or synthetic calcium carbonate with carbon dioxide. The carbon dioxide can be formed in situ by the acid treatment and/or can be supplied from an external source. If a strong acid such as sulphuric acid or hydrochloric acid or medium-strong acid such as phosphoric acid is used for the acid treatment of the natural or synthetic calcium carbonate, the carbon dioxide is automatically formed. Alternatively or additionally, the carbon dioxide can be supplied from an external source.

According to one embodiment, the surface-reacted calcium carbonate is a reaction product of natural or synthetic calcium carbonate with carbon dioxide and at least one acid, wherein the carbon dioxide is formed in situ as a result of contacting the at least one acid with the natural or synthetic calcium carbonate and/or is supplied from an external source.

Acid treatment and treatment with carbon dioxide can be carried out simultaneously which is the case when a strong or medium-strong acid is used. It is also possible to carry out acid treatment first, e.g. with a medium strong acid having a $pK_a$ in the range of 0 to 2.5 at 20° C., wherein carbon dioxide is formed in situ, and thus, the carbon dioxide treatment will automatically be carried out simultaneously with the acid treatment, followed by the additional treatment with carbon dioxide supplied from an external source.

Preferably, the concentration of gaseous carbon dioxide in the suspension is, in terms of volume, such that the ratio (volume of suspension):(volume of gaseous $CO_2$) is from 1:0.05 to 1:20, even more preferably from 1:0.05 to 1:5.

In a preferred embodiment, the acid treatment step and/or the carbon dioxide treatment step are repeated at least once, more preferably several times. According to one embodiment, the at least one acid is added over a time period of at least 30 min, preferably at least 45 min, and more preferably at least 1 h.

Subsequent to the acid treatment and carbon dioxide treatment, the pH of the aqueous suspension, measured at 20° C., naturally reaches a value of greater than 6.0, preferably greater than 6.5, more preferably greater than 7.0, even more preferably greater than 7.5, thereby preparing the surface-reacted calcium carbonate as an aqueous suspension having a pH of greater than 6.0, preferably greater than 6.5, more preferably greater than 7.0, even more preferably greater than 7.5. If the aqueous suspension is allowed to reach equilibrium, the pH is greater than 7. A pH of greater than 6.0 can be adjusted without the addition of a base when stirring of the aqueous suspension is continued for a sufficient time period, preferably 1 hour to 10 hours, more preferably 1 to 5 hours.

Alternatively, prior to reaching equilibrium, which occurs at a pH greater than 7, the pH of the aqueous suspension may be increased to a value greater than 6 by adding a base subsequent to carbon dioxide treatment. Any conventional base such as sodium hydroxide or potassium hydroxide can be used.

Further details about the preparation of the surface-reacted natural calcium carbonate are disclosed in WO 00/39222 and US 2004/0020410, wherein the surface-reacted natural calcium carbonate is described as a filler for paper manufacture. The preparation of surface-reacted calcium carbonate with weak acids is disclosed in EP 2 264 108. The preparation of surface-reacted calcium carbonate and its use in purification processes is disclosed in EP 1 974 806, EP 1 982 759, and EP 1 974 807. The use of surface-reacted calcium carbonate as carrier for the controlled release of active agents is described in WO 2010/037753.

Similarly, surface-reacted precipitated calcium carbonate is obtained. As can be taken in detail from EP 2 070 991, surface-reacted precipitated calcium carbonate is obtained by contacting precipitated calcium carbonate with $H_3O^+$ ions and with anions being solubilised in an aqueous medium and being capable of forming water-insoluble calcium salts, in an aqueous medium to form a slurry of surface-reacted precipitated calcium carbonate, wherein said surface-reacted precipitated calcium carbonate comprises an insoluble, at least partially crystalline calcium salt of said anion formed on the surface of at least part of the precipitated calcium carbonate.

Said solubilised calcium ions correspond to an excess of solubilised calcium ions relative to the solubilised calcium ions naturally generated on dissolution of precipitated calcium carbonate by $H_3O^+$ ions, where said $H_3O^+$ ions are provided solely in the form of a counterion to the anion, i.e. via the addition of the anion in the form of an acid or non-calcium acid salt, and in absence of any further calcium ion or calcium ion generating source.

Said excess solubilised calcium ions are preferably provided by the addition of a soluble neutral or acid calcium salt, or by the addition of an acid or a neutral or acid non-calcium salt which generates a soluble neutral or acid calcium salt in situ.

Said $H_3O^+$ ions may be provided by the addition of an acid or an acid salt of said anion, or the addition of an acid or an acid salt which simultaneously serves to provide all or part of said excess solubilised calcium ions.

According to one embodiment of the present invention, the surface-reacted calcium carbonate is obtained by a process comprising the steps of:
 a) providing a suspension of natural or synthetic calcium carbonate,
 b) adding at least one acid having a $pK_a$ value of 0 or less at 20° C. or having a $pK_a$ value from 0 to 2.5 at 20° C. to the suspension of step a), and
 c) treating the suspension of step a) with carbon dioxide before, during or after step b).

According to one embodiment, at least one acid having a $pK_a$ value of 0 or less at 20° C. is added in step b) to the suspension of step a). According to another embodiment, at least one acid having a $pK_a$ value from 0 to 2.5 at 20° C. is added in step b) to the suspension of step a).

The carbon dioxide used in step c) can be formed in situ by the acid treatment of step b) and/or can be supplied from an external source.

According to one embodiment of the present invention, the surface-reacted calcium carbonate is obtained by a process comprising the steps of:
 A) providing a natural or synthetic calcium carbonate,
 B) providing at least one water-soluble acid,
 C) providing gaseous $CO_2$, D) contacting said natural or synthetic calcium carbonate of step A) with the at least one acid of step B) and with the $CO_2$ of step C), characterised in that:

i) the at least one acid of step B) has a $pK_a$ of greater than 2.5 and less than or equal to 7 at 20° C., associated with the ionisation of its first available hydrogen, and a corresponding anion is formed on loss of this first available hydrogen capable of forming a water-soluble calcium salt, and ii) following contacting the at least one acid with natural or synthetic calcium carbonate, at least one water-soluble salt, which in the case of a hydrogen-containing salt has a $pK_a$ of greater than 7 at 20° C., associated with the ionisation of the first available hydrogen, and the salt anion of which is capable of forming water-insoluble calcium salts, is additionally provided.

The surface-reacted calcium carbonate can be kept in suspension, optionally further stabilised by a dispersant. Conventional dispersants known to the skilled person can be used. A preferred dispersant is polyacrylic acid.

Alternatively, the aqueous suspension described above can be dried, thereby obtaining the solid (i.e. dry or containing as little water that it is not in a fluid form) surface-reacted natural or synthetic calcium carbonate in the form of granules or a powder.

According to one embodiment of the present invention, the surface-reacted calcium carbonate has a specific surface area of from 5 m²/g to 200 m²/g, more preferably 20 m²/g to 80 m²/g and even more preferably 30 m²/g to 60 m²/g, measured using nitrogen and the BET method according to ISO 9277.

The particle size of the surface-reacted calcium carbonate can be tailored with respect to the dentine tubules to be treated. For example, in case of a human molar, wherein the dentine tubules typically have a diameter between 3 and 2 μm, the surface-reacted calcium carbonate particles may have a volume median grain diameter ($d_{50}$) of equal to or less than 3 μm.

According to one embodiment of the present invention, the surface-reacted calcium carbonate is in form of particles having a volume median grain diameter ($d_{50}$) of equal to or less than 3 μm, preferably from 1.5 to 2.9 μm, more preferably from 1.7 to 2.7 μm, and most preferably from 2.2 to 2.6 μm. According to another embodiment of the present invention, the surface-reacted calcium carbonate is in form of particles having a volume determined top cut particle size ($d_{98}$) of equal to or less than 6 μm, preferably from 3.5 to 5.5 μm, and more preferably from 4.5 to 5 μm. According to a preferred embodiment of the present invention, the surface-reacted calcium carbonate is in form of particles having volume median grain diameter ($d_{50}$) of equal to or less than 3 μm, preferably from 1.5 to 2.9 μm, more preferably from 1.7 to 2.7 μm, and most preferably from 2.2 to 2.6 μm, and having a volume determined top cut particle size ($d_{98}$) of equal to or less than 6 μm, preferably from 3.5 to 5.5 μm, and more preferably from 4.5 to 5 μm. The volume median grain diameter ($d_{50}$) and volume determined top cut particle size ($d_{98}$) can be determined by laser diffraction measurements, for example, by using a Malvern Mastersizer 2000.

According to one embodiment of the present invention, the surface-reacted calcium carbonate comprises an insoluble, at least partially crystalline calcium salt of an anion of the at least one acid, which is formed on the surface of the natural or synthetic calcium carbonate. According to one embodiment, the insoluble, at least partially crystalline salt of an anion of the at least one acid covers the surface of the natural or synthetic calcium carbonate at least partially, preferably completely. Depending on the employed at least one acid, the anion may be sulphate, sulphite, phosphate, citrate, oxalate, acetate, formiate and/or chloride.

According to one preferred embodiment, the surface-reacted calcium carbonate is a reaction product of natural calcium carbonate and at least one acid, preferably phosphoric acid.

The surface-reacted calcium carbonate is also capable of associating and transporting an active agent. The association preferably is an adsorption onto the surface of the surface-reacted calcium carbonate particles, be it the outer or the inner surface of the particles or an absorption into the particles, which is possible due to their porosity.

In this respect, it is believed that because of the intra and interpore structure of the surface reacted calcium carbonate, this material is a superior agent to deliver previously ad/ab-sorbed materials over time relative to common materials having similar specific surface areas.

The surface-reacted calcium carbonate may have an intra particle porosity within the range from 5 vol.-% to 50 vol.-%, preferably from 20 vol.-% to 50 vol.-%, and more preferably from 30 vol.-% to 50 vol.-%, calculated from mercury porosimetry measurement. From the bimodal derivative pore size distribution curve the lowest point between the peaks indicates the diameter where the intra and inter-particle pore volumes can be separated. The pore volume at diameters greater than this diameter is the pore volume associated with the inter-particle pores. The total pore volume minus this inter particle pore volume gives the intra particle pore volume from which the intra particle porosity can be calculated, preferably as a fraction of the solid material volume, as described in Transport in Porous Media (2006) 63: 239-259.

Further details with respect to the porosity of the surface-reacted calcium carbonate and its use as agent for delivering materials can be found in WO 2010/037753.

Thus, generally, any agent fitting into the intra- and/or inter particle pores of the surface-reacted calcium carbonate carrier is suitable to be transported by the surface-reacted calcium carbonate carriers according to the invention. For example, active agents such as those selected from the group comprising pharmaceutically active agents, biologically active agents, disinfecting agents, preservatives such as triclosan, flavouring agents, surfactants like defoamers, or additional desensitizing agents can be used. According to one embodiment, at least one active agent is associated with the surface-reacted calcium carbonate. According to a preferred embodiment the active agent is at least one additional desensitizing agent, preferably selected from the group consisting of potassium nitrate, gluteraldehyde, silver nitrate, zinc chloride, strontium chloride hexahydrate, sodium fluoride, stannous fluoride, strontium chloride, strontium acetate, arginine, hydroxyapatite, calcium sodium phosphosilicate, potassium oxalate, calcium phosphate, calcium carbonate, bioactive glasses, and mixtures thereof.

The Oral Care Composition

The oral care composition for the use according to the present invention comprises a surface-reacted calcium carbonate, wherein the surface-reacted calcium carbonate is a reaction product of natural or synthetic calcium carbonate with carbon dioxide and at least one acid.

According to one embodiment of the present invention, the composition comprises from 1 to 20 wt.-%, preferably from 1.5 to 15 wt.-%, more preferably from 2 to 10 wt.-% of the surface-reacted calcium carbonate, based on the total weight of the composition.

The surface-reacted calcium carbonate can consist of only one type of surface-reacted calcium carbonate or can be a mixture of two or more types of surface-reacted calcium carbonate. The oral care composition of the present invention may contain the surface-reacted calcium carbonate as the only desensitizing agent. Alternatively, the oral care composition of the present invention may contain the surface-reacted calcium carbonate in combination with at least one additional desensitising agent. According to one embodiment, the oral care composition comprises at least one additional desensitising agent. Preferably, the additional desensitising agent is selected from the group consisting of potassium nitrate, gluteraldehyde, silver nitrate, zinc chloride, strontium chloride hexahydrate, sodium fluoride, stannous fluoride, strontium chloride, strontium acetate, arginine, hydroxyapatite, calcium sodium phosphosilicate, potassium oxalate, calcium phosphate, calcium carbonate, bioactive glasses, and mixtures thereof.

According to one embodiment, the additional desensitizing agent has a weight median particle size $d_{50}$ from 0.1 to 100 μm, preferably from 0.5 to 50 μm, more preferably from 1 to 20 μm, and most preferably from 2 to 10 μm.

The at least one additional desensitizing agent can be present in the oral care composition in an amount from 1 to 20 wt.-%, preferably from 1.5 to 15 wt.-%, more preferably from 2 to 10 wt.-%, based on the total weight of the composition.

According to one embodiment, the oral care composition of the present invention comprises from 1 to 20 wt.-% of the surface-reacted calcium carbonate and from 1 to 20 wt.-% of an additional desensitising agent, based on the total weight of the composition.

The oral care composition of the present invention can be, for example, a toothpaste, a toothpowder, a varnish, an adhesive gel, a cement, a resin, a spray, a foam, a balm, a composition carried out on a mouthstrip or a buccal adhesive patch, a chewable tablet, a chewable pastille, a chewable gum, a lozenge, a beverage, or a mouthwash. According to one embodiment of the present invention, the oral care composition is a toothpaste, a toothpowder, or a mouthwash, and preferably a toothpaste.

According to a preferred embodiment, the oral care composition is a toothpaste, a toothpowder, or a mouthwash and the surface-reacted calcium carbonate is a reaction product of natural or synthetic calcium carbonate with carbon dioxide and phosphoric acid. According to another preferred embodiment, the oral care composition is a toothpaste, a toothpowder, or a mouthwash and the surface-reacted calcium carbonate is a reaction product of natural or synthetic calcium carbonate with carbon dioxide and phosphoric acid, wherein the surface-reacted calcium carbonate is in form of particles having a volume median grain diameter ($d_{50}$) of equal to or less than 3 μm, preferably from 1.5 to 2.9 μm, more preferably from 1.7 to 2.7 μm, and most preferably from 2.2 to 2.6 μm, and/or having a volume determined top cut particle size ($d_{98}$) of equal to or less than 6 μm, preferably from 3.5 to 5.5 μm, and more preferably from 4.5 to 5 μm.

The surface-reacted calcium carbonate can consist of one type of surface-reacted calcium carbonate or can be a mixture of two or more types of surface-reacted calcium carbonate. According to one embodiment, the surface-reacted calcium carbonate has a radioactive dentine abrasion (RDA) value of less than 70, preferably less than 50, and more preferably less than 35. According to one embodiment of the present invention, the oral care composition is a toothpaste for sensitive teeth and/or for children's teeth, and preferably the surface-reacted calcium carbonate has an RDA of less than 50, and most preferably less than 35.

According to one embodiment of the present invention, the oral care composition has a pH between 7.5 and 10, preferably between 8 and 9.

According to one embodiment of the present invention, the oral care composition comprises a surface-reacted calcium carbonate, wherein the surface-reacted calcium carbonate is a reaction product of natural or synthetic calcium carbonate with carbon dioxide and at least one acid, and wherein the surface-reacted calcium carbonate is in form of particles having a volume determined top cut particle size ($d_{98}$) of equal to or less than 6 μm.

In addition to the surface-reacted calcium carbonate and the optional additional desensitizing agent, the oral care composition may further comprise bioadhesive polymers, fluoride compounds, surfactants, binders, humectants, remineralisers, flavouring agents, sweetening agents and/or water.

According to one embodiment of the present invention, the oral care composition comprises a bioadhesive polymer. The bioadhesive polymer may include any polymer that promotes adhesion of the surface-reacted calcium carbonate to teeth or tooth surface and remains on the teeth or tooth surface for an extended period of time, for example, 1 hour, 3 hours, 5 hours, 10 hours, 24 hours. In certain embodiments, the bioadhesive polymer may become more adhesive when the oral care composition is moistened with, for example, water or saliva. In other embodiments, the bioadhesive polymer is a material or combination of materials that enhance the retention of the active ingredient on the teeth or a tooth surface onto which the composition is applied. Such bioadhesive polymers include, for example, hydrophilic organic polymers, hydrophobic organic polymers, silicone gums, silicas, and combinations thereof. According to one embodiment, the bioadhesive polymer is selected from the group consisting of hydroxyethyl methacrylate, PEG/PPG copolymers, polyvinylmethylether/maleic anhydride copolymers, polyvinylpyrrolidone (PVP), cross-linked PVP, shellac, polyethylene oxide, methacrylates, acrylates copolymers, methacrylic copolymers, vinylpyrrolidone/vinyl acetate copolymers, polyvinyl caprolactum, polylactides, silicone resins, silicone adhesives, chitosan, milk proteins (casein), amelogenin, ester gum, and combinations thereof.

Examples of suitable fluoride compounds are sodium fluoride, stannous fluoride, sodium monofluorophosphate, potassium fluoride, potassium stannous fluoride, sodium fluorostannate, stannous chlorofluoride and amine fluoride. The fluoride compounds may be added in an amount from 0.1 to 2 wt.-%, based on the total weight of the oral care composition. Good results can be achieved employing an amount of fluoride compound to provide available fluoride ion in the range of 300 to 2 000 ppm in the oral care composition, preferably about 1 450 ppm.

Suitable surfactants are generally anionic organic synthetic surfactants throughout a wide pH range. Representative of such surfactants used in the range of about 0.5 to 5 wt.-%, based on the total weight of the oral care composition, are water-soluble salts of $C_{10}$-$C_{18}$ alkyl sulphates, such as sodium lauryl sulphate, of sulphonated monoglycerides of fatty acids, such as sodium monoglyceride sulphonates, of fatty acid amides of taurine, such as sodium N-methyl-N-palmitoyltauride, and of fatty acid esters of isethionic acid, and aliphatic acylamides, such as sodium N-lauroyl sarcosinate. However, surfactants obtained from natural sources such as cocamidopropyl betaine may also be used.

Suitable binders or thickening agents to provide the desired consistency are, for example, hydroxyethylcellulose, sodium carboxymethylcellulose, natural gums, such as gum karaya, gum arabic, gum tragacanth, xanthan gum or cellulose gum, colloidal silicates, or finely divided silica. Generally, from 0.5 to 5 wt.-%, based on the total weight of the oral care composition, can be used.

Various humectants known to the skilled person can be used, such as glycerine, sorbitol and other polyhydric alcohols, for example, in an amount from 20 to 40 wt.-%, based on the total weight of the oral care composition. Examples of suitable flavouring agents include oil of wintergreen, oil of spearmint, oil of peppermint, oil of clove, oil of sassafras and the like. Saccharin, aspartame, dextrose, or levulose can be used as sweetening agents, for example, in an amount from 0.01 to 1 wt.-%, based on the total weight of the oral care composition. Preservatives such as sodium benzoate may be present in an amount from 0.01 to 1 wt.-%, based on the total weight of the oral care composition. Colorants such as titanium dioxide may also be added to the oral care composition, for example, in an amount from 0.01 to 1 wt.-%, based on the total weight of the oral care composition.

The oral care composition of the present invention may also contain a material selected from the group consisting of silica, precipitated silica, alumina, aluminosilicate, metaphosphate, tricalcium phosphate, calcium pyrophosphate, ground calcium carbonate, precipitated calcium carbonate, sodium bicarbonate, bentonite, kaolin, aluminium hydroxide, calcium hydrogen phosphate, hydroxylapatite, and mixtures thereof. According to one embodiment, the oral care composition contains a material being selected from ground calcium carbonate and/or precipitated silica. According to another embodiment, the oral care composition contains a material being selected from the group consisting of ground calcium carbonate, precipitated calcium carbonate, aluminium hydroxide, calcium hydrogen phosphate, silica, hydroxylapatite, and mixtures thereof. According to a preferred embodiment of the present invention, the oral care composition comprises surface-reacted calcium carbonate, wherein the surface-reacted calcium carbonate is a reaction product of natural or synthetic calcium carbonate with carbon dioxide and at least one acid, and calcium carbonate, preferably ground calcium carbonate and/or precipitated calcium carbonate.

According to one embodiment of the present invention, the oral care composition is a tooth paste. The toothpaste may be produced by a method comprising the following steps:
I) providing a mixture of water and a humectants, and optionally at least one of a thickener, a preservative, a fluoride, and a sweetener,
II) adding a surface-reacted calcium carbonate, and optionally a colorant, to the mixture of step I), wherein the surface-reacted calcium carbonate is a reaction product of natural or synthetic calcium carbonate with carbon dioxide and at least one acid,
III) adding a surfactant to the mixture of step II), and
IV) optionally, adding a flavouring agent to the mixture of step III).

However, a toothpaste of the present invention may also be produced by any other method known to the skilled person.

Therapeutic Use

It was found that surface-reacted calcium carbonate can be used in therapy, and especially in dental therapy. According to the present invention, a surface-reacted calcium carbonate for use as a medicament is provided, wherein the surface-reacted calcium carbonate is a reaction product of natural or synthetic calcium carbonate with carbon dioxide and at least one acid. According to a further aspect of the present invention, an oral care composition for use as a medicament is provided, comprising a surface-reacted calcium carbonate, wherein the surface-reacted calcium carbonate is a reaction product of natural or synthetic calcium carbonate with carbon dioxide and at least one acid.

According to one embodiment, the surface-reacted calcium carbonate of the present invention or the oral care composition of the present invention is used in treating dentine hypersensitivity.

The inventors of the present invention surprisingly found that surface-reacted calcium carbonate is useful in therapy, for example, dental therapy, and especially in the treatment of dentine hypersensitivity. Surface-reacted calcium carbonate differs from conventional calcium carbonate in several aspects. For example, unlike conventional calcium carbonate, surface-reacted calcium carbonate comprises a porous, platy or lamellar surface structure (see FIGS. 1 and 2). Without being bound to any theory, it is believed that due to its porous platy or lamellar surface structure, the surface-reacted calcium carbonate can occlude the dentine tubules without cutting of the diffuse flow of nutrients into the dentine tubules. It is also believed that due to its special surface-structure, the surface-modified calcium carbonate can interlock in the dentine tubules by a mechanism of canting due to its lamellar surface structure, and thus, can remain within the tubules for a long time period. Furthermore, the surface treatment renders the surface-reacted calcium carbonate more resistant against acids. Therefore, the surface-reacted calcium carbonate is more stable under acidic conditions, for example, during consumption of acidic beverages such as soft drinks or acidic dishes such as salads with vinegar-based dressings.

The surface-reacted calcium carbonate of the present invention and/or oral compositions comprising the same may be used in professional, in-office treatment or in at home treatment.

According to one embodiment, the surface-reacted calcium carbonate for use in treating dentine hypersensitivity is used in a method comprising administering to at least one tooth of a patient a therapeutically effective amount of the surface-reacted calcium carbonate at least once a day, preferably twice a day and more preferably three-times a day. A "therapeutically effective" amount of the surface-reacted calcium carbonate is an amount that is sufficient to have the desired therapeutic or prophylactic effect in the human subject to whom the active agent is administered, without undue adverse side effects (such as toxicity, irritation, or allergic response), commensurate with a reasonable benefit/risk ratio when used in the manner of this invention. The specific effective amount will vary with such factors as the particular condition being treated, the physical condition of the subject, the nature of concurrent therapy (if any), the specific dosage form, the oral care composition employed, and the desired dosage regimen.

According to one embodiment, the oral composition for use in treating dentine hypersensitivity is used in a method comprising applying the composition to at least one tooth of a patient for an effective amount of time, preferably the composition remains on the at least one tooth for at least 1 min, at least 15 min, at least 30 min, at least 1 hour, at least 2 hours, at least 12 hours or at least 24 hours.

The scope and interest of the present invention will be better understood based on the following figures and examples which are intended to illustrate certain embodiments of the present invention and are non-limitative.

EXAMPLES

1. Measurement Methods

Figure 1:
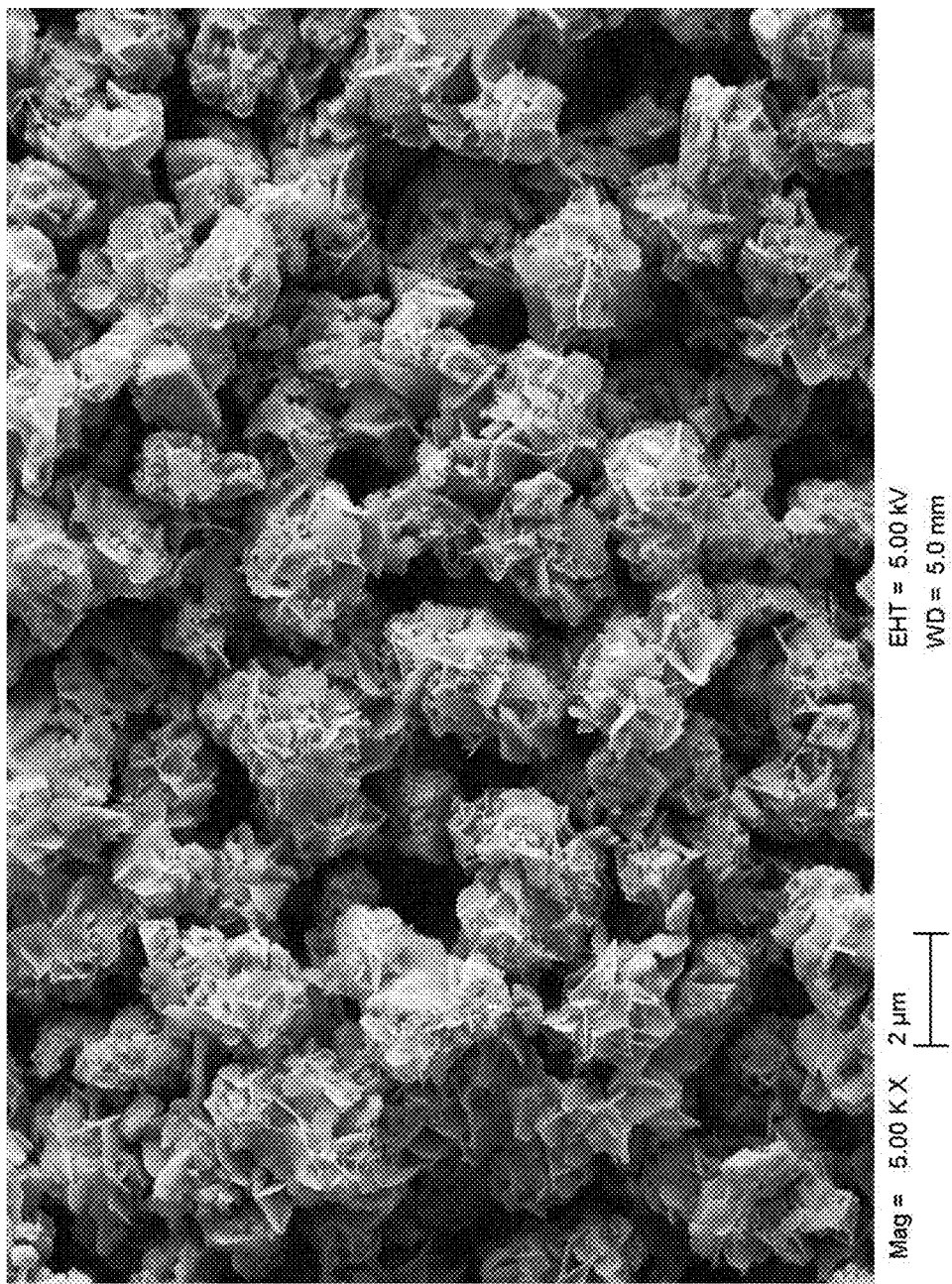
FIG. 1 shows a scanning electron microscope (SEM) micrograph of the surface-reacted calcium carbonate prepared according to Example 1.

In the following, measurement methods implemented in the examples are described.

Particle Size Distribution

The particle size distribution of non surface-reacted calcium carbonate particles, e.g., ground calcium carbonate, was measured using a Sedigraph 5100 from the company Micromeritics, USA. The method and the instrument are known to the skilled person and are commonly used to determine grain size of fillers and pigments. The measurement was carried out in an aqueous solution comprising 0.1 wt.-% $Na_4P_2O_7$. The samples were dispersed using a high speed stirrer and supersonics. For the measurement of dispersed samples, no further dispersing agents were added.

The volume median grain diameter ($d_{50}$) of surface-reacted calcium carbonate was determined using a Malvern Mastersizer 2000 Laser Diffraction System (Malvern Instruments Plc., Great Britain).

Scanning Electron Microscope (SEM) Micrographs

The prepared surface-reacted calcium carbonate and the tooth neck samples were examined by a Sigma VP field emission scanning electron microscope (Carl Zeiss AG, Germany) and a variable pressure secondary electron detector (VPSE) with a chamber pressure of about 50 Pa.

Specific Surface Area (SSA)

The specific surface area is measured via the BET method according to ISO 9277 using nitrogen, following conditioning of the sample by heating at 250° C. for a period of 30 minutes. Prior to such measurements, the sample is filtered within a Büchner funnel, rinsed with deionised water and dried overnight at 90 to 100° C. in an oven. Subsequently the dry cake is ground thoroughly in a mortar and the resulting powder placed in a moisture balance at 130° C. until a constant weight is reached Solids Content of an Aqueous Suspension The suspension solids content (also known as "dry weight") was determined using a Moisture Analyser MJ33 from the company Mettler-Toledo, Switzerland, with the following settings: drying temperature of 160° C., automatic switch off if the mass does not change more than 1 mg over a period of 30 sec, standard drying of 5 to 20 g of suspension.

2. Examples

Example 1—Preparation of Surface-Reacted Calcium Carbonate

In a mixing vessel, 7 liters of an aqueous suspension of ground calcium carbonate was prepared by adjusting the solids content of a ground calcium carbonate having a particle size distribution of 90 wt.-% below 2 µm, based on the total weight of the ground calcium carbonate, (commercially available from Omya AG, Switzerland) such that a solids content of 15 wt.-%, based on the total weight of the aqueous suspension, is obtained. 232 g phosphoric acid was added in form of an aqueous solution containing 30 wt.-% phosphoric acid to said suspension over a period of 30 minutes at a temperature of 70° C. After addition of acid, the slurry was stirred for additional 5 minutes, before removing from the vessel.

The resulting surface-reacted calcium carbonate had a volume median grain diameter ($d_{50}$) of 2.7 µm, as measured by laser diffraction (Malvern Mastersizer 2000), and a specific surface area of 51.0 m²/g.

A SEM micrograph of the surface-reacted calcium carbonate having a porous platy or lamellar surface structure is shown in FIG. 1.

Example 2—Preparation of Surface-Reacted Calcium Carbonate

In a mixing vessel, 7 liters of an aqueous suspension of ground calcium carbonate was prepared by adjusting the solids content of a ground calcium carbonate having a particle size distribution of 90 wt.-% below 2 µm, based on the total weight of the ground calcium carbonate, (commercially available from Omya AG, Switzerland) such that a solids content of 20 wt.-%, based on the total weight of the aqueous suspension, is obtained.

320 g phosphoric acid was added in form of an aqueous containing 30 wt.-% phosphoric acid to said suspension over a period of 60 minutes at a temperature of 70° C. After addition of acid, the slurry was stirred for additional 5 minutes, before removing from the vessel.

The resulting surface-reacted calcium carbonate had a volume median grain diameter ($d_{50}$) of 2.4 µm, as measured by laser diffraction (Malvern Mastersizer 2000), and a specific surface area of 48.8 m²/g.

Figure 2:
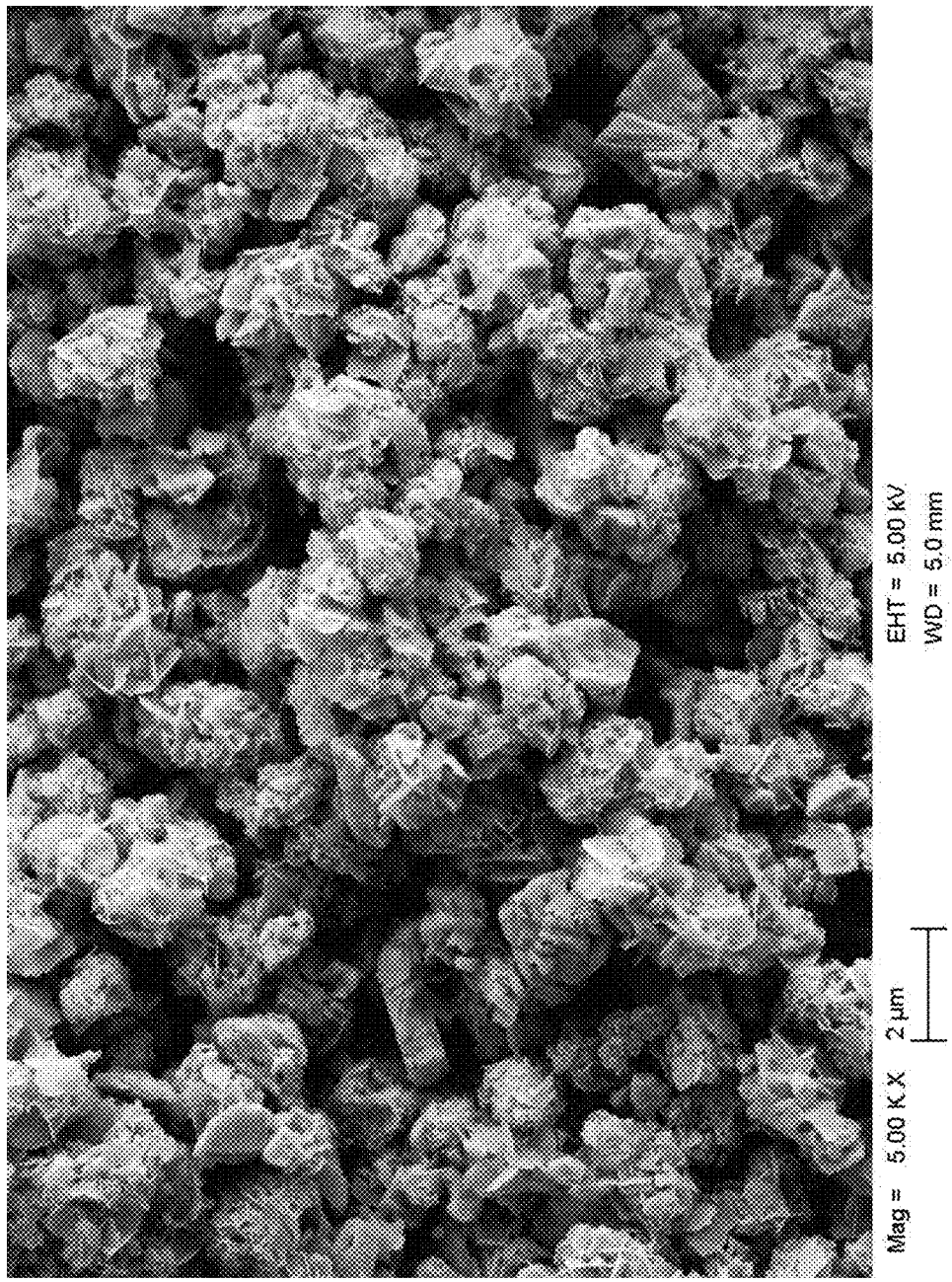
FIG. 2 shows a SEM micrograph of the surface-reacted calcium carbonate prepared according to Example 2.

A SEM micrograph of the surface-reacted calcium carbonate having a porous platy or lamellar surface structure is shown in FIG. 2.

Example 3—Preparation of Surface-Reacted Calcium Carbonate

In a mixing vessel, 7 liters of an aqueous suspension of ground calcium carbonate was prepared by adjusting the solids content of a ground calcium carbonate having a particle size distribution of 90 wt.-% below 2 µm, based on the total weight of the ground calcium carbonate, (commercially available from Omya AG, Switzerland) such that a solids content of 20 wt.-%, based on the total weight of the aqueous suspension, is obtained.

320 g phosphoric acid was added in form of an aqueous solution containing 30 wt.-% phosphoric acid to said suspension over a period of 60 minutes at a temperature of 85° C. After addition of acid, the slurry was stirred for additional 5 minutes, before removing from the vessel.

The resulting surface-reacted calcium carbonate had a volume median grain diameter ($d_{50}$) of 2.1 μm, as measured by laser diffraction (Malvern Mastersizer 2000), and a specific surface area of 20.2 m$^2$/g.

Example 4—Tooth Treatment with Surface-Reacted Calcium Carbonate

The crown section of a bovine molar was separated from the tooth neck by a saw. Subsequently, the following grinding and polishing steps were carried out on the tooth neck using a Buehler Phoenix 4000 polishing machine (Buehler GmbH, Germany):

Firstly, the tooth neck was grinded parallel to its longitudinal axis until the dentine layer has been reached (grinding wheel: Ultraprep 20 μm, velocity: 300 rpm, water-cooling). Subsequently, the pre-grinded surface was polished for 30 s (grinding wheel: Apex, velocity: 300 rpm, water-cooling). Finally, the polished surface was further polished for 120 with a polishing cloth (Texmet perforated, velocity: 150 rpm, no water-cooling).

The polished tooth neck was soaked for 2 min in a 15% EDTA solution and rinsed with tap water.

The prepared tooth neck sample was soaked in the surface-reacted calcium carbonate suspensions of Example 1, 2 or 3 for 60 s and the tooth surface was brushed for 30 s with a tooth brush. Subsequently, the tooth sample was rinsed with tap water.

The tooth neck samples before and after treatment with surface-reacted calcium carbonate were glued onto a SEM sample holder and examined by a Sigma VP field emission scanning electron microscope (Carl Zeiss AG, Germany) and a variable pressure secondary electron detector (VPSE) with a chamber pressure of about 50 Pa.

Figure 3:
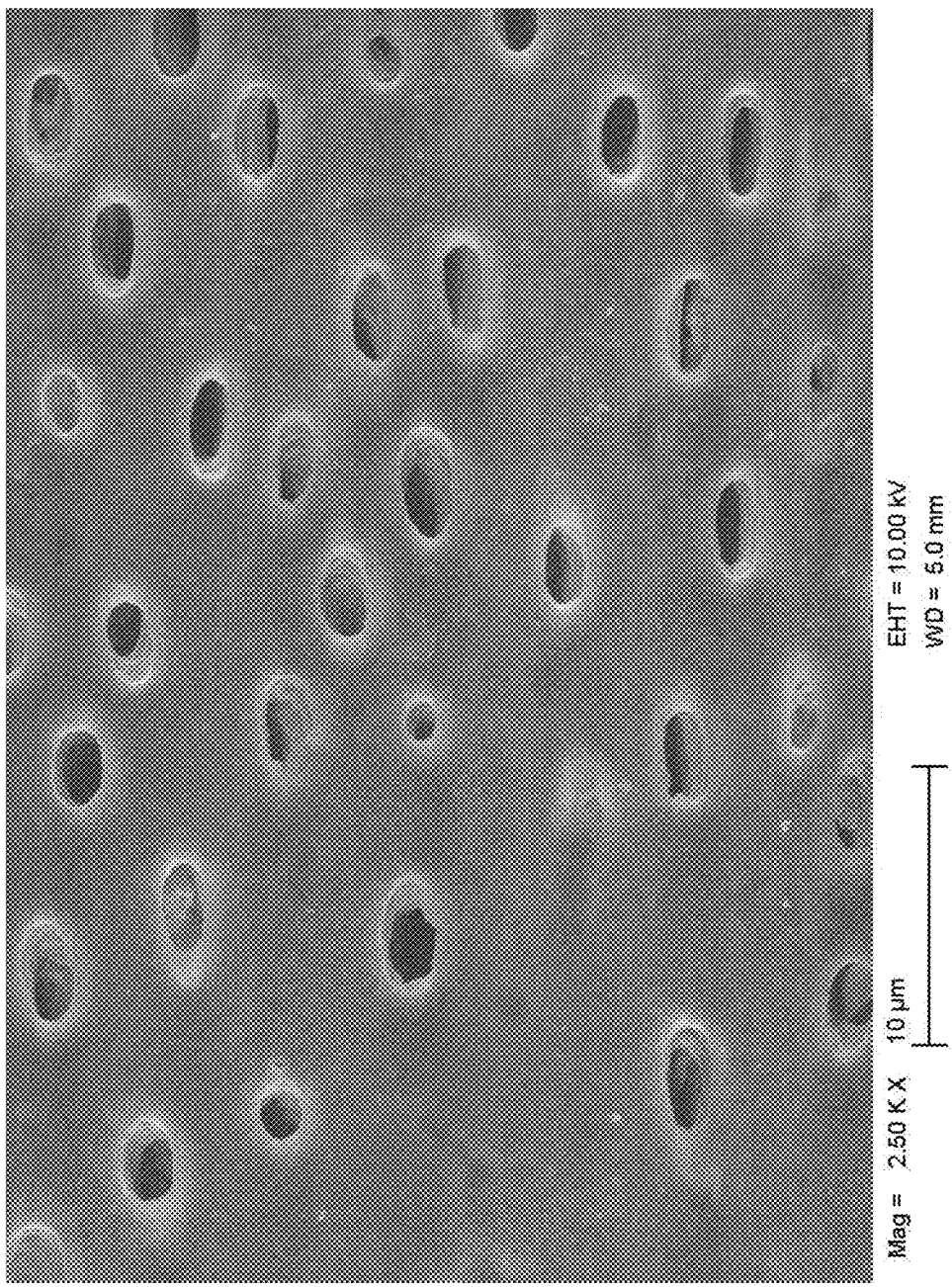
FIG. 3 shows a SEM micrograph of an untreated bovine tooth neck sample with open dentinal tubules.
Figure 4:
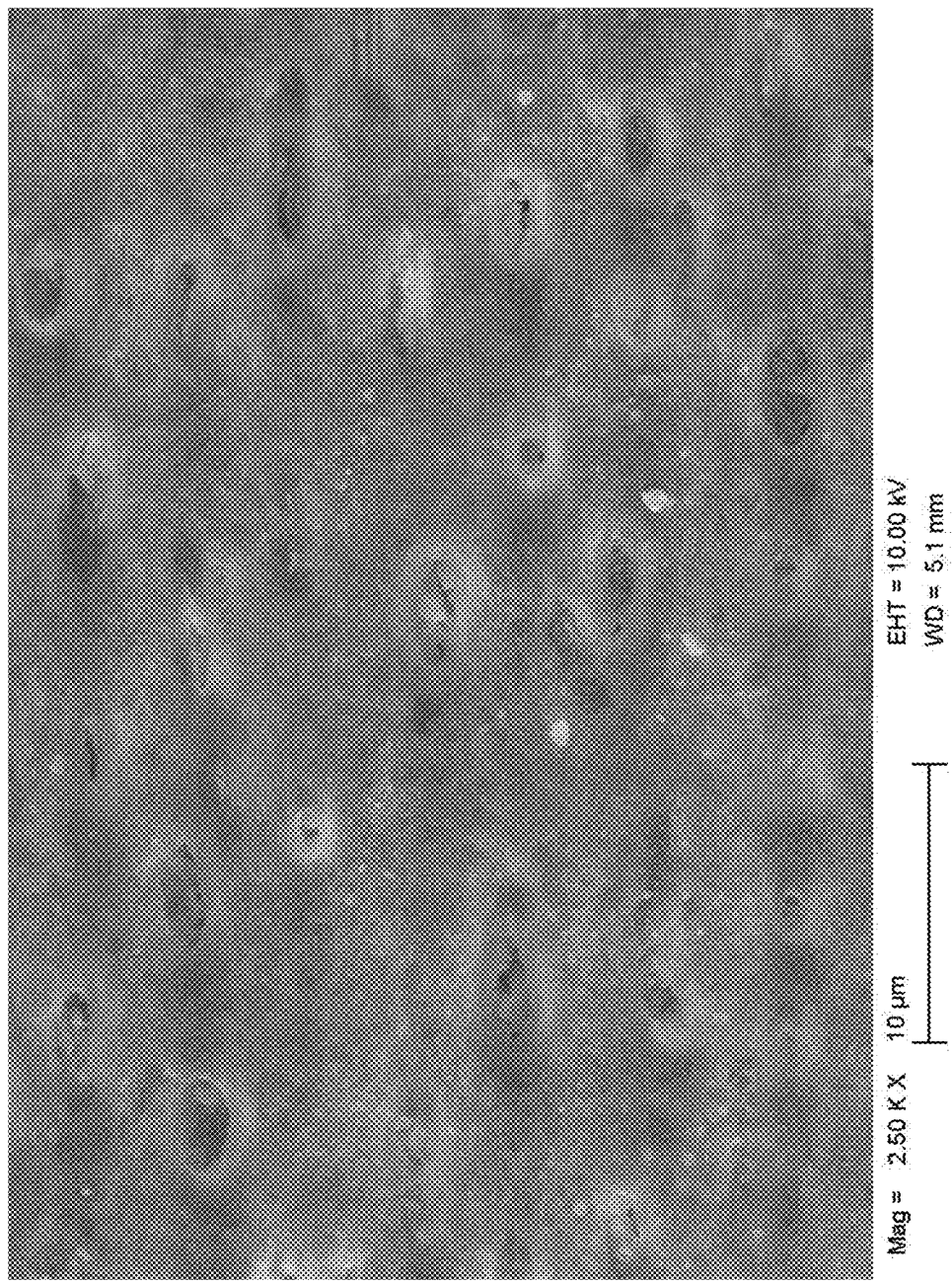
FIG. 4 shows a SEM micrograph of a bovine tooth neck sample that was treated with the surface-reacted calcium carbonate of Example 1.

FIG. 3 shows a scanning electron microscope (SEM) micropgraphs of the untreated tooth neck sample and FIG. 4 shows a SEM micrograph of a tooth neck sample, which was treated with the suspension of surface-reacted calcium carbonate of Example 1. While the open dentine tubules are clearly visible in the untreated sample shown in FIG. 3, FIG. 4 evidences that the dentine tubules have been effectively occluded by the treatment with the inventive suspension of surface-reacted calcium carbonate.

Example 5—Resistance to Acid Challenge

A bovine tooth neck sample was prepared by treating a bovine tooth neck with surface-reacted calcium carbonate of Example 3 according to the procedure set out in Example 4. The obtained tooth neck sample was soaked for 10 s in a 0.2 M acetic acid solution. Subsequently, the tooth neck sample was rinsed with tap water.

As comparative example, a bovine tooth neck sample was prepared as described in Example 4, but by using a ground calcium carbonate from Avenza-Carrara, Italy (weight median particle size $d_{50}$=2.6 μm, commercially available from Omya AG, Switzerland) instead of surface-reacted calcium carbonate.

The tooth neck samples before and after treatment with acetic acid were glued onto a SEM sample holder and examined by a Sigma VP field emission scanning electron microscope (Carl Zeiss AG, Germany) and a variable pressure secondary electron detector (VPSE) with a chamber pressure of about 50 Pa.

Figure 5:
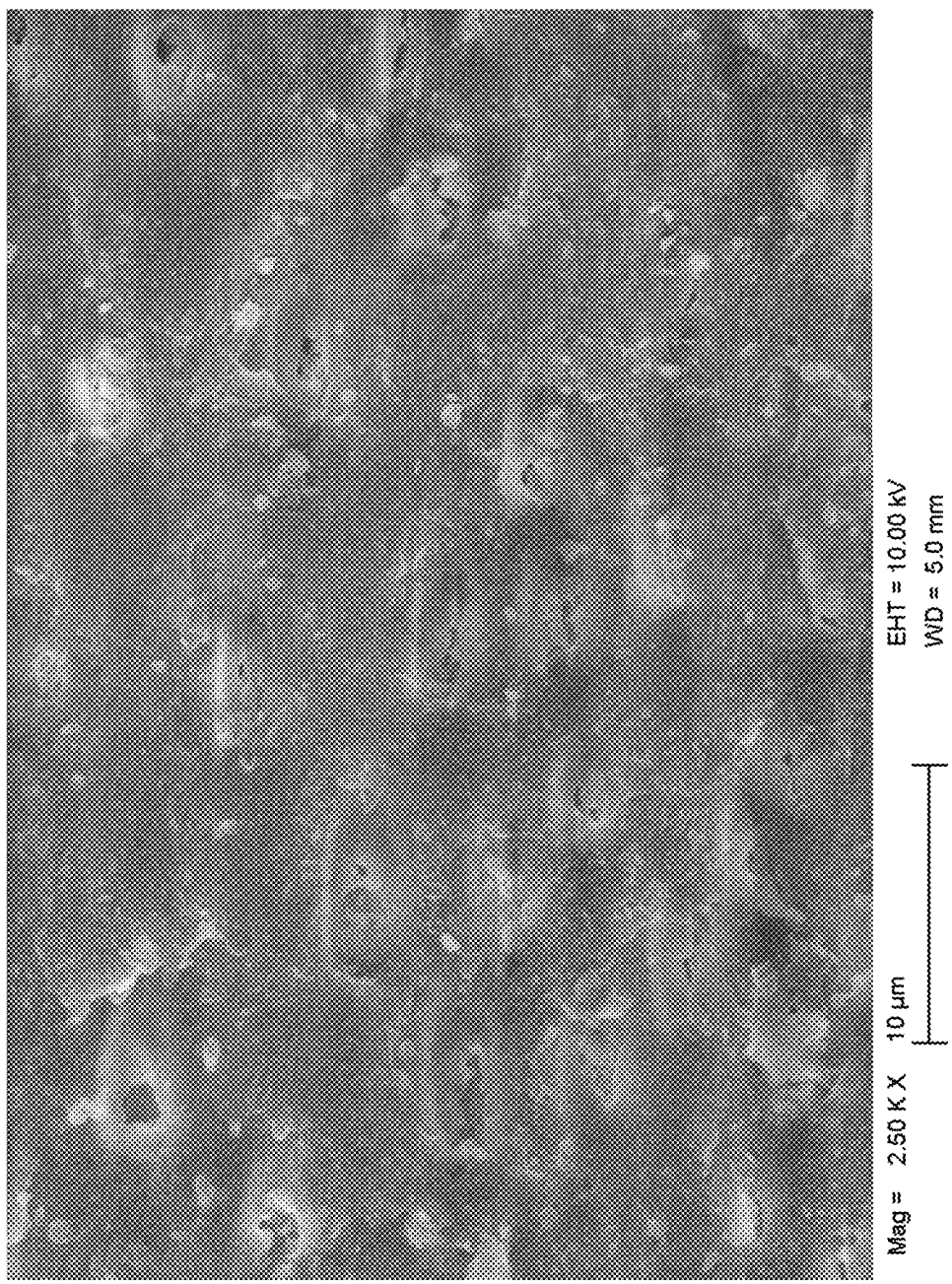
FIG. 5 shows a SEM micrograph of a bovine tooth neck sample that was treated with the surface-reacted calcium carbonate of Example 3.
Figure 6:
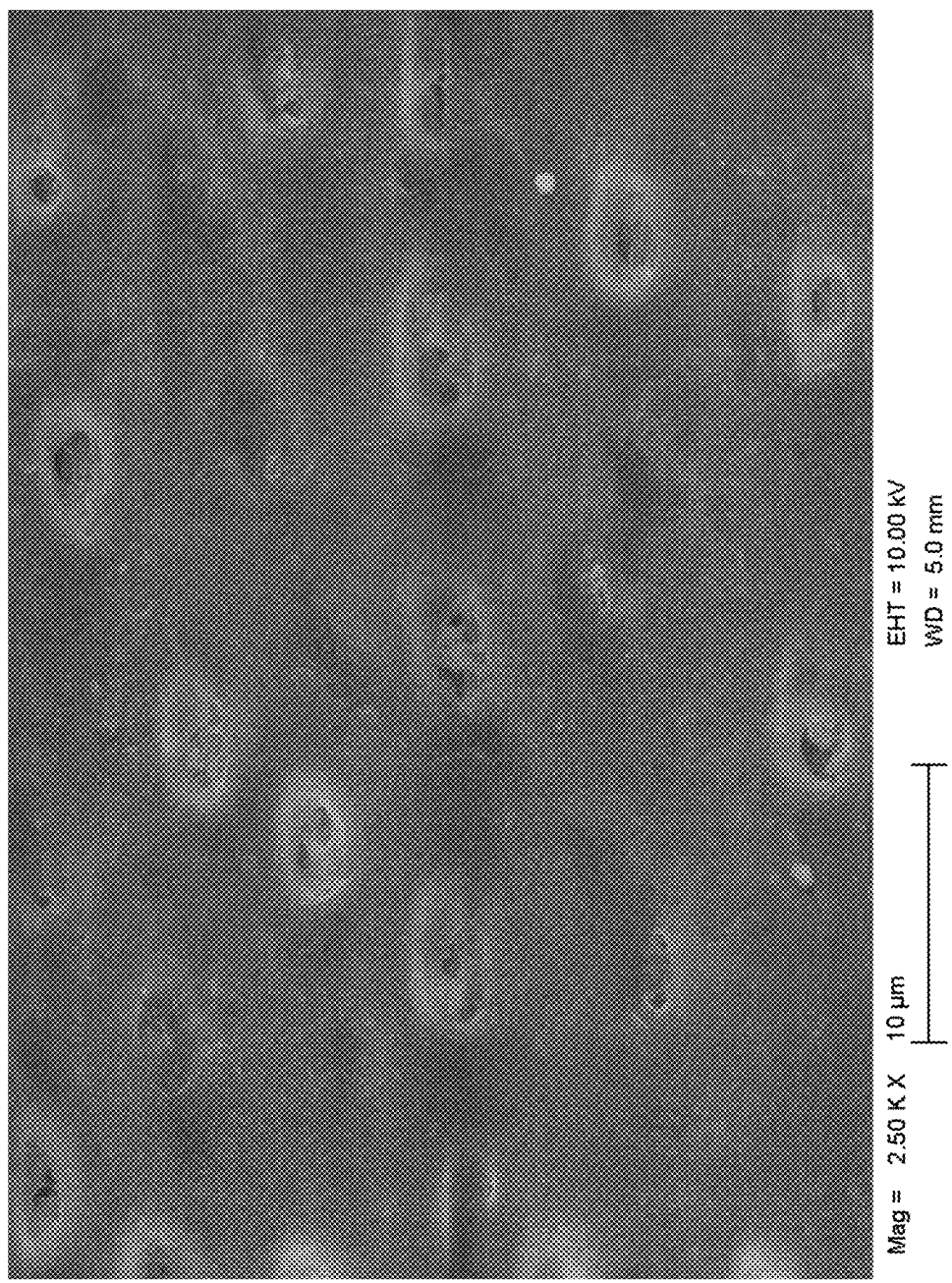
FIG. 6 shows a SEM micrograph of a bovine tooth neck sample that was treated with the surface-reacted calcium carbonate of Example 3 and a 0.2 M acetic acid solution.
Figure 7:
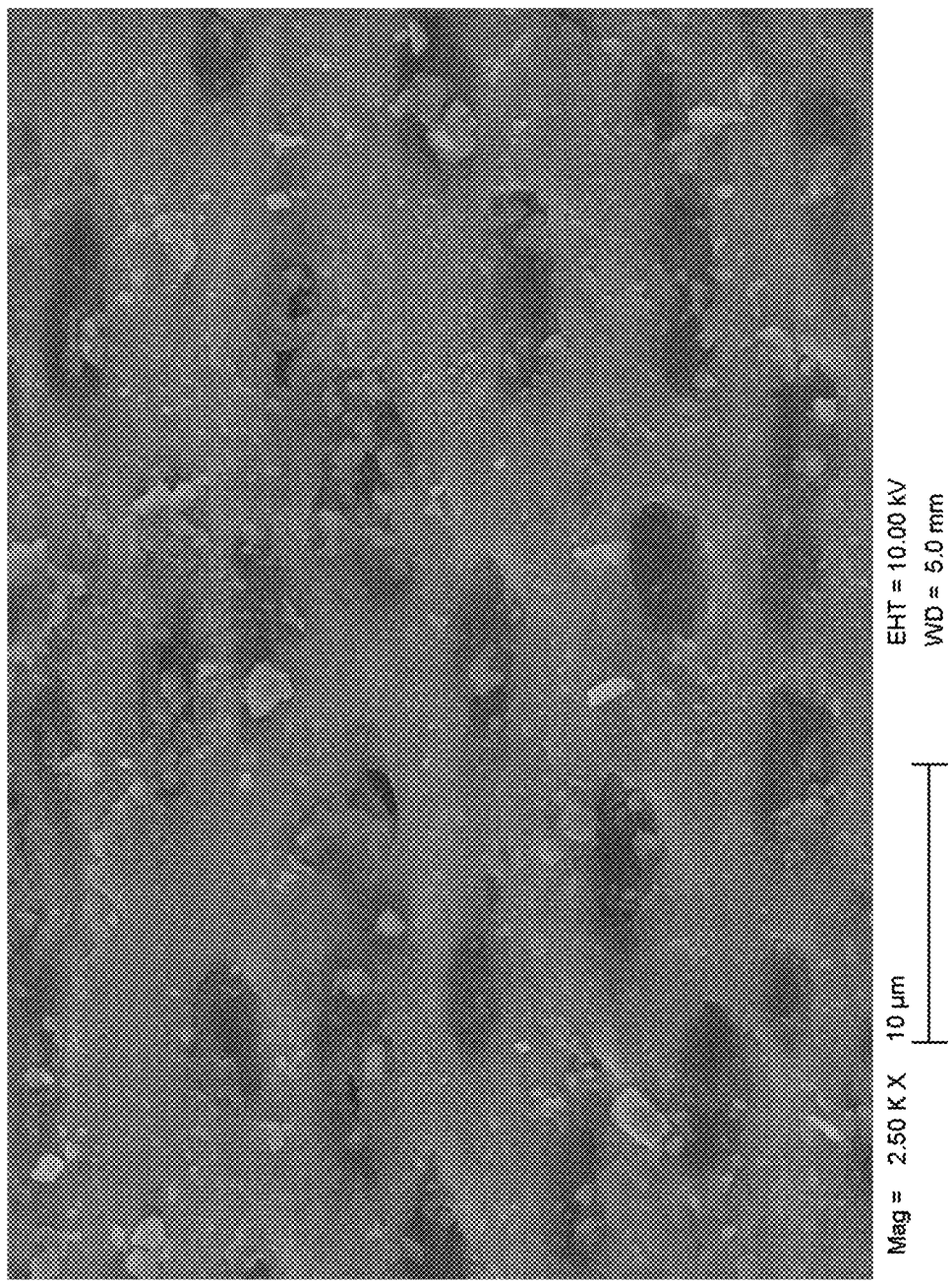
FIG. 7 shows a SEM micrograph of a bovine tooth neck sample that was treated with a ground calcium carbonate (comparative example).
Figure 8:
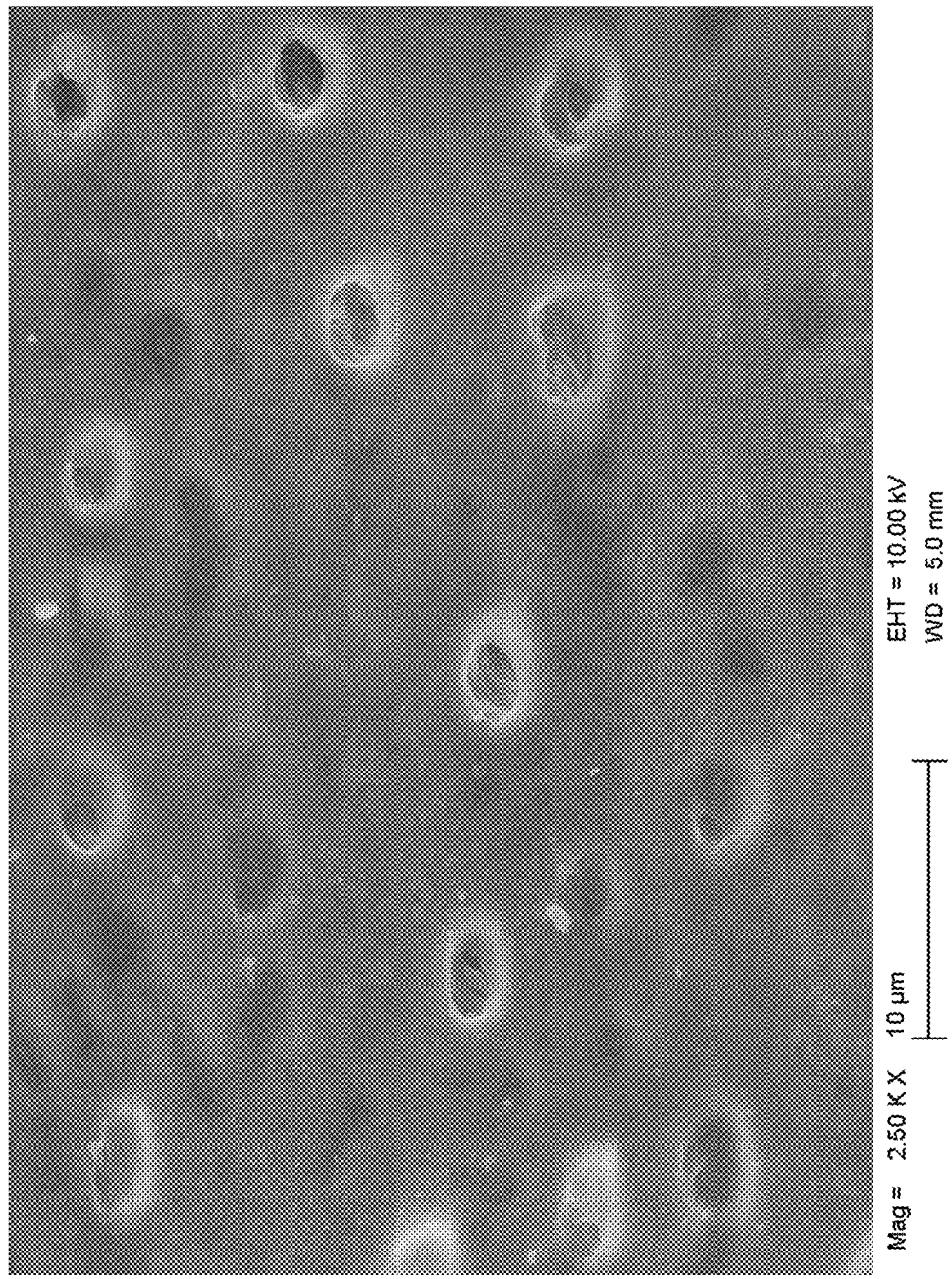
FIG. 8 shows a SEM micrograph of a bovine tooth neck sample that was treated with a ground calcium carbonate (comparative example) and a 0.2 M acetic acid solution.

FIG. 5 shows a scanning electron microscope (SEM) micrograph of a tooth neck sample being treated with the inventive surface-reacted calcium carbonate of Example 5 before the acid treatment and FIG. 6 shows a SEM micrograph of such a tooth neck sample after acid treatment. FIG. 7 shows a scanning electron microscope (SEM) micrograph of a tooth neck sample being treated with the comparative ground calcium carbonate before the acid treatment and FIG. 8 shows a SEM micrograph of such a tooth neck sample after acid treatment. While the occluded dentine tubules are clearly visible for the inventive sample in FIG. 5, FIG. 7 evidences that by using the comparative ground calcium carbonate the dentine tubules are only occluded partially or are not occluded at all. Furthermore, it can be gathered from FIG. 8 that the comparative ground calcium carbonate has been removed from the tooth surface and the dentine tubules almost completely by the acid treatment. In contrast, the inventive sample shown in FIG. 6 shows that the dentine tubules are still occluded by the inventive surface-reacted calcium carbonate after the acid treatment. These results demonstrate that the inventive surface-reacted calcium carbonate is resistant to an acid challenge from a typical beverage or dish that may be consumed following use of the product.

The invention claimed is:

1. A method for treating dentine hypersensitivity in a subject comprising contacting teeth of the subject with an oral care composition comprising a surface-reacted calcium carbonate in an amount effective to treat dentine hypersensitivity, wherein the surface-reacted calcium carbonate is a reaction product of natural calcium carbonate with carbon dioxide and phosphoric acid in an aqueous suspension, wherein the carbon dioxide is formed in situ by phosphoric acid treatment, and wherein the surface-reacted calcium carbonate is in a form of particles having a volume median grain diameter (d50) of from 1.5 to 2.9 μm and a volume determined top cut particle size (d98) of less than or equal to 6 μm.

2. The method according to claim 1, wherein the surface-reacted calcium carbonate is in a form of particles having a volume determined top cut particle size (d98) of from 3.5 to 5.5 μm.

3. The method according to claim 1, wherein the surface-reacted calcium carbonate is in a form of particles having a volume median grain diameter (d50) of from 1.7 to 2.7 μm and/or a volume determined top cut particle size (d98) of from 4.5 to 5 μm.

4. The method according to claim 1, wherein the surface-reacted calcium carbonate is in a form of particles having a volume median grain diameter (d50) of from 2.2 to 2.6 μm and/or a volume determined top cut particle size (d98) of from 4.5 to 5 μm.

5. The method according to claim 1, wherein the surface-reacted calcium carbonate is in a form of particles having a specific surface area of from 5 m$^2$/g to 200 m$^2$/g, measured using nitrogen and the BET method according to ISO 9277.

6. The method according to claim 1, wherein the surface-reacted calcium carbonate is in a form of particles having a specific surface area of from 20 m$^2$/g to 80 m$^2$/g, measured using nitrogen and the BET method according to ISO 9277.

7. The method according to claim 1, wherein the surface-reacted calcium carbonate is in a form of particles having a specific surface area of from 30 m²/g to 60 m²/g, measured using nitrogen and the BET method according to ISO 9277.

8. The method according to claim 1, wherein the oral care composition further comprises at least one active agent.

9. The method according to claim 8, wherein the active agent is a desensitizing agent.

10. The method according to claim 1, wherein the oral care composition comprises from 1 to 20 wt.-% of the surface-reacted calcium carbonate, based on the total weight of the composition.

11. The method according to claim 1, wherein the oral care composition comprises from 2 to 10 wt.-% of the surface-reacted calcium carbonate, based on the total weight of the composition.

12. The method according to claim 1, wherein the oral care composition is a toothpaste, a toothpowder, or a mouthwash.

13. The method according to claim 1, wherein the oral care composition further comprises an agent selected from the group consisting of potassium nitrate, gluteraldehyde, silver nitrate, zinc chloride, strontium chloride hexahydrate, sodium fluoride, stannous fluoride, strontium chloride, strontium acetate, arginine, hydroxylapatite, calcium sodium phosphosilicate, potassium oxalate, calcium phosphate, calcium carbonate, a bioactive glass, and any mixture thereof.

14. The method according to claim 1, wherein the oral care composition further comprises a bioadhesive polymer.

15. The method according to claim 14, wherein the bioadhesive polymer is selected from the group consisting of hydroxyethyl methacrylate, PEG/PPG copolymers, polyvinylmethyl ether/maleic anhydride copolymers, polyvinylpyrrolidone (PVP), cross-linked PVP, shellac, polyethylene oxide, methacrylates, acrylates copolymers, methacrylic copolymers, vinylpyrrolidone/vinyl acetate copolymers, polyvinyl caprolactum, polylactides, silicone resins, silicone adhesives, chitosan, milk proteins, casein, amelogenin, ester gum, and any combination thereof.

16. The method according to claim 1, wherein the surface-reacted calcium carbonate has a radioactive dentine abrasion (RDA) value of less than 70.

17. The method according to claim 1, wherein the surface-reacted calcium carbonate has a radioactive dentine abrasion (RDA) value of less than 50.

18. The method according to claim 1, wherein the surface-reacted calcium carbonate has a radioactive dentine abrasion (RDA) value of less than 35.

19. The method according to claim 1, wherein the oral care composition has a pH between 7.5 and 10.

20. The method according to claim 1, wherein the oral care composition has a pH between 8 and 9.

* * * * *

UNITED STATES PATENT AND TRADEMARK OFFICE
CERTIFICATE OF CORRECTION

PATENT NO. : 10,463,693 B2  
APPLICATION NO. : 15/123034  
DATED : November 5, 2019  
INVENTOR(S) : Gerard et al.

Page 1 of 1

It is certified that error appears in the above-identified patent and that said Letters Patent is hereby corrected as shown below:

In the Claims

In Column 21, Line 21, in Claim 13, delete "gluteraldehyde," and insert --glutaraldehyde,-- therefor In Column 22, Line 10, in Claim 15, delete "caprolactum," and insert --caprolactam,-- therefor Signed and Sealed this
Seventh Day of July, 2020

Andrei Iancu
*Director of the United States Patent and Trademark Office*